United States Patent [19]

Matier et al.

[11] 4,402,974
[45] Sep. 6, 1983

[54] METHOD FOR TREATING GLAUCOMA BY THE TOPICAL ADMINISTRATION OF SELECTIVELY METABOLIZED BETA-BLOCKING AGENTS

[75] Inventors: William L. Matier, Liberty; Sheung-Tsam Kam, Vernon Hills, both of Ill.

[73] Assignee: American Hospital Supply Corporation, Evanston, Ill.

[21] Appl. No.: 276,657

[22] Filed: Jun. 23, 1981

[51] Int. Cl.³ .................... C07C 69/76; A01N 37/10; A61K 31/235
[52] U.S. Cl. .................................. 424/308; 424/307; 424/309; 560/66; 560/67; 560/110
[58] Field of Search .................. 560/66, 110, 67; 424/307, 308, 309

[56] References Cited

U.S. PATENT DOCUMENTS 3,959,351 5/1976 Day et al. ........................... 560/110
4,127,674 0/0000 Leopold ............................... 560/66
4,195,085 0/0000 Stone ................................... 560/66

FOREIGN PATENT DOCUMENTS 3664 6/1979 European Pat. Off. .
2373513 of 0000 France ................................. 560/66

OTHER PUBLICATIONS

Physicians' Desk Reference, Charles E. Baker, Jr., 35th Edition, 1232-1234 (1981).
W. P. Boger, Drugs, 18, 25-32 (1979).
L. Bonomi et al., Glaucoma, Eds. R. Pitts Corck and A. D. S. Caldwell, Academic Press, New York, pp. 99-105 (1980).
Demmler, Forshr. Med. 98 Jg (1980), Nr. 23, pp. 880-885.
Heel et al., Drugs, 17 38-55 (1979).
Krieglstein et al., Albrecht v. Graefes Arch. klin. exp. Opthal., 202, 81-86 (1977).
P. Vareilles et al., Investigative Ophthalmology and Visual Science, vol. 16/11, 987 (1977).
T. Zimmerman, Drug Therapy, Jul. 1979, pp. 87-89.
T. J. Zimmerman and W. P. Boger, Surv. Ophthalmol. Buechi, O. Melal, C. A., vol. 68 (1968) 76664u.

Primary Examiner—Paul J. Killos
Attorney, Agent, or Firm—Bernard, Rothwell & Brown

[57] ABSTRACT

A method for the treatment of glaucoma or lowering intraocular pressure in a mammal, involving topically administering to the eye of such mammal a selectively metabolized beta-blocking compound of the formula

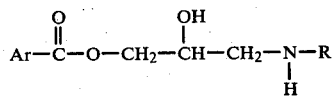

wherein R may be lower alkyl, lower hydroxyalkyl, lower alkynyl, aralkyl, or an ester-containing group and Ar may be substituted or unsubstituted aromatic; or a pharmaceutically acceptable salt thereof. Because of a relatively long duration of action of such compounds in ocular fluids and a relatively short duration of action in the systemic circulation, such compounds are useful for the treatment of excessive intraocular pressure without substantial systemic effects.

15 Claims, No Drawings

METHOD FOR TREATING GLAUCOMA BY THE TOPICAL ADMINISTRATION OF SELECTIVELY METABOLIZED BETA-BLOCKING AGENTS

BACKGROUND OF THE INVENTION

The present invention relates to a method for the treatment of glaucoma. More particularly, the invention relates to a novel method of treatment of glaucoma or lowering of intraocular pressure by topically administering beta-adrenergic blocking agents to the eye.

Glaucoma is a condition of the eye characterized by increased intraocular pressure. Untreated, the condition can eventually lead to irreversible retinal damage and blindness. Conventional therapy for glaucoma has involved topical administration of pilocarpine and/or epinephrine, administered to the eye several times daily.

Various beta-blocking agents may also be used to lower intraocular pressure. Such use is described, for example, in reviews by W. P. Boger in *Drugs*, 18, 25-32 (1979) and by T. J. Zimmerman and W. P. Boger in *Survey Ophthalmol.* 23(b), 347 (1979). The use of beta-blockers for the treatment of glaucoma is also described in the patent literature. For example, U.S. Pat. No. 4,195,085 to Stone discloses a method for treatment of glaucoma by the ocular administration of a beta-blocking compound, timolol maleate. U.S. Pat. No. 4,127,674 discloses treating glaucoma with labetalol, a known antagonist of both alpha and beta adrenergic receptors. However, these methods also possess significant drawbacks, in that the absorption of the beta-blocking compound into the systemic circulation can cause undesirable side effects. Such side effects result from prolonged beta-blocking action on the heart, bronchioles and blood vessels. For example, according to *Physicians' Desk Reference*, Charles E. Baker, Jr., 35th Edition, 1981, p. 1233, adverse reactions to the topical use of timolol maleate can include bronchospasm, heart failure, as well as cardiac conduction defects. Accordingly, there is a need for a method of treatment of glaucoma or for lowering intraocular pressure which is relatively free of unwanted systemic side-effects.

Certain beta-blocking agents which contain enzymatically labile ester groups are known to exhibit short-acting beta-blocking effects in the systemic circulation. Such short-acting beta-blocking compounds (SAABs) have been suggested for treatment or prophylaxis of cardiac disorders as a means for reducing heart work or improving rhythmicity for a short duration. Such short-acting beta-blocking compounds avoid the sometimes counterproductive effects of conventional beta-blocking agents, whose effects are long-lived and therefore difficult to precisely control.

SUMMARY OF THE INVENTION

In accordance with the present invention, disclosed herein is a method for the treatment of glaucoma or for lowering intraocular pressure in a mammal, comprising topically administering to the eye of such mammal a beta-blocking compound of the formula:

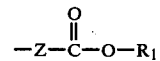

wherein R represents lower alkyl of straight or branched carbon chains from 1 to about 10 carbon atoms; cycloalkyl of from 3 to about 7 carbon atoms; alkenyl of from about 2 to about 10 carbon atoms; alkynyl of from 3 to about 10 carbon atoms; hydroxyalkyl of from 2 to about 7 carbon atoms; aralkyl, wherein the alkyl portion contains from 1 to about 5 carbon atoms, and the aryl portion represents substituted or unsubstituted monocyclic or polycyclic aromatic or heterocyclic ring systems of from about 6 to about 10 carbon atoms; a group of the formula

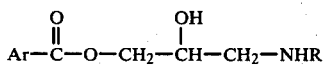

wherein Z represents lower alkylene of straight or branched carbon chains of from 1 to about 10 carbon atoms, and $R_1$ is lower alkyl of from 1 to about 5 carbon atoms; and Ar represents substituted or unsubstituted aromatic; or a pharmaceutically-acceptable salt thereof.

DETAILED DESCRIPTION OF THE INVENTION

The above-mentioned short-acting beta-blocking compounds effectively reduce intraocular pressure in the eyes of mammals when topically administered. Because of their short-lived duration of action in the systemic circulation, toxic side-effects produced by their migration out of the eye are consequently reduced. It has further been discovered that certain of these compounds show an increased longevity of effect when present in the ocular fluid compared to the duration of their systemic effects. Consequently, the present invention resides in the treatment of glaucoma or lowering intraocular pressure with a beta-blocking compound which exhibits relatively long duration of action while in the ocular fluid, but which is subject to relatively rapid breakdown into inactive metabolites upon passage to the systemic circulation.

Compounds administered by the method of the present invention are represented by the formula:

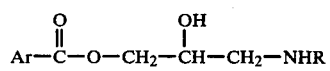

wherein R represents lower alkyl of straight or branched carbon chains from 1 to about 10 carbon atoms; cycloalkyl of from 3 to about 7 carbon atoms; alkenyl of from 2 to about 10 carbon atoms; alkynyl of from 2 to about 10 carbon atoms; hydroxyalkyl of from 2 to about 7 carbon atoms; aralkyl, wherein the alkyl portion contains from about 1 to about 5 carbon atoms and the aryl portion represents substituted or unsubstituted monocyclic or polycyclic aromatic or heterocyclic ring systems of from 6 to about 10 carbon atoms, such as benzyl, phenethyl, 3,4-dimethoxyphenethyl, 1,1-dimethyl-2-(3-indolyl) ethyl, and the like; and Ar represents substituted or unsubstituted aromatic, including monocyclic, polycyclic and heterocyclic ring systems. Aromatic (Ar) substituents may include lower alkyl, lower alkenyl, lower alkynyl, lower alkoxy, halogen, acetamido, amino, nitro, lower alkylamino, hydroxy, hydroxyalkyl, cyano, methylenedioxy, acyloxy, wherein the acyl portion is a straight or branched chain alkanoyl of from 1 to about 7 carbon atoms or aroyl of from 6 to about 10 carbon atoms, optionally substituted by halogen, lower alkoxy, lower alkyl, acetamido, cyano or hydroxy, and groups of the formula

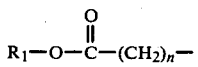

wherein $R_1$ is lower alkyl, aryl or aralkyl and n is an integer from 0 to about 10. The compounds described herein are not limited to any particular stereoisomeric configuration. Such compounds may be administered as their pharmaceutically acceptable acid addition salts, e.g., as the hydrochloride, sulfate, phosphate, oxalate, gluconate, tartrate, et cetera.

In preferred compounds R is lower alkyl of from 1 to about 5 carbon atoms, such as isopropyl, n-butyl, t-butyl, n-pentyl, and the like; alkynyl of from 3 to about 5 carbon atoms, such as propargyl, dimethylpropargyl and the like; hydroxyalkyl of from 2 to about 5 carbon atoms, such as hydroxy-t-butyl and the like; or aralkyl wherein the alkyl portion contains from 1 to about 3 carbon atoms and the aryl portion contains from 6 to about 10 carbon atoms, such as benzyl, phenethyl, 3,4-dimethoxyphenethyl and the like; and Ar is unsubstituted phenyl, or phenyl substituted with lower alkyl of from 1 to about 5 carbon atoms, fluoro, chloro, nitro, hydroxy, amino, acyloxy, wherein the acyl portion is alkanoyl of from 2 to about 5 carbon atoms, or benzoyl optionally substituted by halogen, alkoxy, alkyl or hydroxy, or a group of the formula

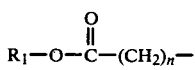

wherein $R_1$ is lower alkyl of from 1 to about 5 carbon atoms, and n is an integer from 0 to about 5. In particularly preferred embodiments of the present invention, R is selected from the group consisting of isopropyl, t-butyl, hydroxy-t-butyl, dimethylpropargyl, and 3,4-dimethoxyphenethyl, and Ar is unsubstituted phenyl or phenyl substituted with methyl, fluoro, chloro, nitro, hydroxy, amino, acyloxy such as acetoxy, isobutyryloxy, pivaloyloxy, benzoyloxy or 4-methoxybenzoyloxy.

The compounds described herein may be prepared by a number of synthethic methods, depending upon the particular structure desired.

Compounds of the invention may be advantageously prepared by either of the following two methods:

Method I:

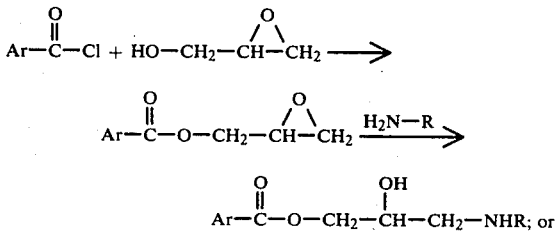

Method II:

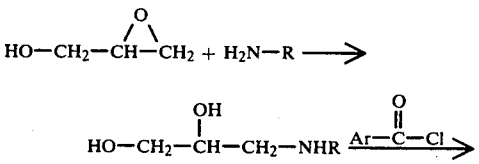

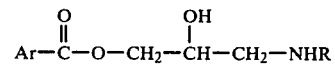

The latter method is particularly preferred for compounds in which R is an ester-containing group.

The compounds of this invention are advantageously administered topically to the eye in the form of a solution, ointment, or solid insert such as is described in U.S. Pat. No. 4 195,085. Formulations may contain the active compound preferably, in the form of a soluble acid addition salt, in amounts ranging from about 0.01% to about 10% by wt., preferably, from about 0.5% to about 5% by wt. Unit dosages of the active compound can range from about 0.001 to about 5.0 mg., preferably from about 0.05 to about 2.0 mg. The dosage administered to a patient will depend upon the patient's needs and the particular compounds employed.

Carriers used in the preparations of the present invention are preferably non-toxic pharmaceutical organic or inorganic compositions such as water; mixtures of water and water-miscible solvents, such as lower alcohols; mineral oils; petroleum jellies; ethyl cellulose; polyvinylpyrrolidone and other conventional carriers. In addition, the pharmaceutical preparations may also contain additional components such as emulsifying, preserving, wetting and sterilizing agents. These include polyethylene glycols 200, 300, 400 and 600, carbowaxes 1,000, 1,500, 4,000, 6,000 and 10,000, bacteriocidal components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The method of treatment of this invention advantageously involves the topical administration of eye drops containing the active compound. Formulations for eye drops preferably include the active compound as a soluble acid addition salt in a properly buffered, sterile, aqueous isotonic solution.

The compounds of the present invention are ester group-containing beta-blockers that have a selective, localized, beta-blocking effect in the eye after topical administration. Such compounds are thought to be rapidly metabolized by plasma and/or liver esterases into inactive by-products, upon entering the systemic circulation. It has been discovered that these same compounds are relatively stable in ocular fluids, i.e., lacrimal fluids and aqueous humor. Consequently, such compounds are useful for the treatment of glaucoma or for lowering intraocular pressure since they remain stable when topically applied to the eye but rapidly metabolize when subsequently absorbed into the systemic circulation.

Some of the compounds break down in the aqueous humor more rapidly than others. Such compounds may advantageously be employed when only a temporary reduction in intraocular pressure is desired, say for diagnostic procedures. Longer-acting compounds are generally used for effecting longer-term reductions in intraocular pressure, such as is desired when treating chronic glaucoma. Thus, the method of the present invention provides a very useful therapeutic alternative for the treatment of glaucoma or for lowering intraocular pressure.

The in vitro studies hereinafter described indicate that the compounds used in the method of the present invention will undergo different rates of enzymatic hydrolysis depending on their location within the body (See Table I). For example, compound of Example III is completely hydrolyzed within 60 minutes in both dog blood and liver homogenate while only 19% hydrolyzed after one hour in aqueous humor, and only 51.9% hydrolyzed after two hours. Compound of Example IV is less stable in aqueous humor, hydrolyzing 61.4% after one hour, 100% after two hours.

The present invention is further illustrated by the following examples which are not intended to be limiting.

EXAMPLE I

This example describes the synthesis of a compound of the formula:

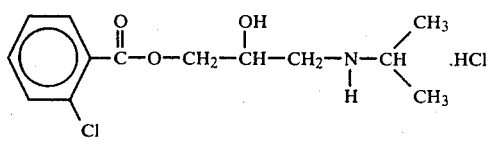

2,3Epoxypropyl-2-chlorobenzoate

A mixture containing 14.8 g (0.2 mole) of glycidol, 150 ml of anhydrous ether, 16 g (0.4 mole) of pyridine and 35.2 g (0.2 mole) of 2-chlorobenzoyl chloride was stirred at room temperature for two hours. The mixture was filtered and the ether was evaporated to leave an oil. This oil was distilled to give a colorless oil. The NMR and IR spectra were consistent with the assigned structure.

[3-(Isopropylamino)-2-hydroxy]propyl 2-chlorobenzoate hydrochloride

To 1 g of the epoxide from the previous experiment were added 10 g of isopropylamine. The resultant solution was refluxed for 16 hours and evaporated to dryness. The oily residue was chromatographed on a column (silica gel/EtOH:CH$_2$Cl$_2$=1.5:3.5) to yield the free amine product. The amine was converted to its HCl salt by addition of ethereal HCl. The amine salt was collected by filtration and recrystallized in 2-propanol to give white crystals: m.p. 129° C. The NMR and IR spectra were consistent with the assigned structure and the elemental analysis was consistent with the empirical formula $C_{13}H_{26}O_3NCl_2$.

EXAMPLE Ia

This example describes an alternate synthesis of the compound of Example I.

3-(Isopropylamino)-1,2-propanediol

A mixture of 37 g (0.5 mole) of glycidol and 35.4 g (0.6 mole) of isopropylamine was stirred at 25° C. overnight. Excess isopropylamine was evaporated in vacuo and the mixture was distilled to give 53 g of product: b.p. 80° C./0.1 mm Hg. The NMR and IR spectra were consistent with the assigned structure and the elemental analysis was consistent with the empirical formula $C_6H_{15}O_2N$.

[3-(Isopropylamino)-2-hydroxy]propyl 2-chlorobenzoate hydrochloride

A solution of 10 g (75 mmole) of the diol from the previous experiment and 5.9 g (75 mmole) of pyridine hydrochloride in 20 ml of pyridine was treated with 13.1 g (75 mmole) of 2-chlorobenzoyl chloride. The mixture was stirred at room temperature for two hours and 100 ml of water was added. The pyridine was evaporated in vacuo at 55°-60° C. and the aqueous solution was washed with 100 ml of ether. The aqueous layer was then basified with K$_2$CO$_3$ and extracted with methylene chloride. The methylene chloride layer was acidified with ether-HCl and evaporated to dryness. The residue was crystallized in 2-propanol to give 12.5 g (54%) of product: m.p. 129° C.

EXAMPLE II

This example describes the synthesis of a compound of the formula:

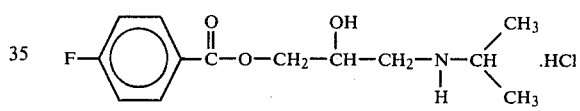

The experiment of Example Ia was repeated in all essential details to produce the above compound, except the reactant 4-fluorobenzoyl chloride was substituted for 2-chlorobenzoyl chloride. The compound was prepared as the acid addition salt. The compound was identified by NMR and IR spectroscopy, elemental analysis, and had a melting point of 139°-140° C.

EXAMPLE III

This example describes the synthesis of a compound of the formula:

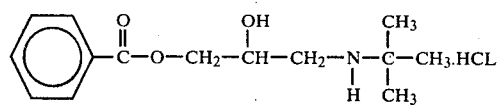

The experiment of Example Ia was repeated in all essential details to produce the above compound, except the reactants t-butylamine and benzoyl chloride were substituted for isopropylamine and 2-chlorobenzoyl chloride, respectively. The compound was prepared as the acid addition salt. The compound was identified by NMR and IR spectroscopy, elemental analysis, and had a melting point of 105°-106° C.

EXAMPLE IV

This example describes the synthesis of a compound of the formula:

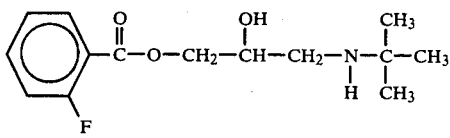

The experiment of Example Ia was repeated in all essential details to produce the above compound, except the reactants t-butylamine and 2-fluorobenzoyl chloride were substituted for isopropylamine and 2-chlorobenzoyl chloride, respectively. The compound was prepared as the free base. The compound was identified by NMR and IR spectroscopy, elemental analysis, and had a melting point of 97.5°–98° C.

EXAMPLES V–VIII

The enzymatic hydrolysis rates of the compounds of Examples I–IV were examined in dog blood, liver homogenate, and aqueous humor. All of the compounds tested were synthesized in accordance with the previous examples. Acetonitrile was "HPLC" grade. Distilled water was used to dissolve the compounds and 0.01 N HCl was used to dissolve compounds requiring an acidic pH for dissolution.

Fresh aqueous humor was collected from eyes of dogs using a 23 gauge needle while fresh dog blood was collected into heparinized Vacutainer ® tubes. Fresh liver was homogenized in 0.9% NaCl using a Potter-Elvehjem Teflon pestle and glass homogenizer making a 25% (W/V) homogenate.

A 0.5 ml aliquot of dog aqueous humor, blood, or liver homogenate was incubated with 12.5 μg (0.5 ml) of beta-blocker in a Dubnoff shaking metabolic incubator at 37° C. for 60 and 120 minutes. Denatured tissue controls were prepared by adding 2.0 ml of acetonitrile into 0.5 ml of aqueous humor, blood, or liver homogenate to destroy esterase activities prior to addition of the beta-blockers. These controls were then incubated at 37° C. for 120 minutes. After 60 and 120 minutes, the incubations were terminated by addition of 2 ml of acetonitrile and immediately mixed using a Vortex ® mixer to stop esterase activities.

All samples were centrifuged at 4000 RPM for 10 minutes to sediment denatured proteins. The resultant supernatants were transferred to WISP ® vials and analyzed by high pressure liquid chromatography. The hydrolysis of beta-blockers in aqueous humor, blood, and liver homogenate was determined by disappearance of the compounds. The extent of enzymatic hydrolysis in each tissue was determined by comparing the amount of each compound (absolute peak area) recovered at each time point to the amount of each compound (absolute peak area) in denatured tissue control and aqueous control samples.

All of the compounds examined were initially tested for chemical hydrolysis in 0.1 N potassium phosphate buffer, pH 7.40, and all were found to be stable for at least three hours (data not shown).

Table 1 summarizes the results of these experiments. The extent of hydrolysis is expressed in terms of the amount of each compound recovered after the incubation period relative to the amount of each compound recovered in the denatured tissue control. Most of the beta-blockers were hydrolyzed very rapidly (≧90% in 120 minutes) when incubated with dog blood and liver homogenate. In contrast, all of the compounds tested were resistant to enzymatic hydrolysis by esterases in dog aqueous humor having hydrolysis rates of 19–61% in 60 minutes and 52–100% in 120 minutes.

EXAMPLE IX

This example describes the synthesis of a compound of the formula:

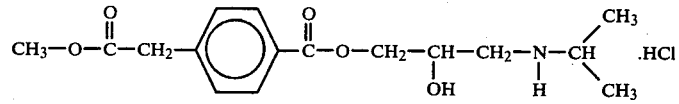

2,3 Epoxypropyl 4-[(Methoxycarbonyl)methyl]benzoate

A mixture containing 14.8 g (0.2 mole) of glycidol, 150 ml of anhydrous ether, 16 g (0.4 mole of pyridine and 43 g (0.2 mole) of 4-[(methoxycarbonyl)methyl]benzoyl chloride is stirred at room temperature for two hours. The mixture is filtered and the ether evaporated to leave an oil. This oil is distilled to give a colorless oil.

[3-(Isopropylamino)-2-hydroxy]propyl 4-[(methoxycarbonyl)methyl]benzoate Hydrochloride To 1.6 g of the epoxide from the previous experiment is added 10 g of isopropylamine. The resultant solution is refluxed for 16 hours and evaporated to dryness. The oily residue is chromatographed on a column (silica gel/EtOH:CH₂Cl₂=1.5:3.5) to the free amine product. The amine was converted to its HCl salt by addition of ethereal HCl. The amine salt was collected by filtration and recrystallized in 2-propanol to give white crystals.

EXAMPLE X

This example describes the synthesis of a compound of the formula:

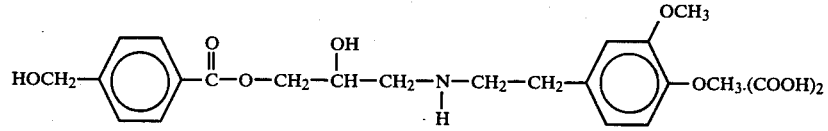

3-[N-[(4-methoxybenzyl)oxycarbonyl]-N-(3,4-dimethoxyphenethyl)]amino-1,2-propanediol A mixture of 26 g (0.102 mole) of 3-(3,4-dimethoxyphenethyl)amino-1,2-propanediol, 29 g (0.345 mole) of sodium bicarbonate and 24 g (0.116 mole) of p-methoxybenzyloxycarbonyl azide in 200 ml of dioxane and 10 ml of water was stirred at room temperature for 24 hours. After evaporation of the dioxane in vacuo, the residue was partitioned between water and CHCl₃.

Evaporation of CHCl₃ gave an oil which was purified by chromatography (silica gel/10% ethanol in methylene chloride) to give 13 g (30.5%) of product.

[2-Hydroxy-3-[[N-[(4-Methoxybenzyl)oxycarbonyl]-N-(3,4-dimethoxyphenethyl)]amino]propyl]4-formylbenzoate The diol from the previous experiment was allowed to react with 4-formylbenzoyl chloride in a similar manner as described in the preparation of [2-Hydroxy-3-(isopropylamino)]propyl 2-chlorobenzoate hydrochloride in Example II. The product was purified by chromatography (silica gel/2% ethanol in ether). The yield was 27%.

[2-Hydroxy-3-[(3,4-dimethoxyphenethyl)amino]-propyl]4-(hydroxymethyl) benzoate oxalate The aldehyde obtained from the previous experiment was dissolved in ethanol. The resulting solution was cooled to 0° C. and sodium borohydride in a molar amount equal to the molar amount of the aldehyde was added. The reaction mixture was stirred at 0° C. for ten minutes and excess hydride was destroyed by addition of water. The crude product was dissolved in ether-HCl and stirred at room temperature for two hours. The ether was evaporated to dryness and the product was partitioned between 5% $K_2CO_3$ and methylene chloride. A solution of oxalic acid in 2-propanol was added to the methylene chloride layer and the precipitate was recrystallized in ethanol to give the desired product in 19% yield; m.p. 164°–164.5° C. The NMR and IR spectra were consistent with the assigned structure and the elemental analysis was consistent with the empirical formula $C_{23}H_{29}NO_{10}$.

EXAMPLE XI

This example describes the synthesis of a compound of the following formula via Method I.

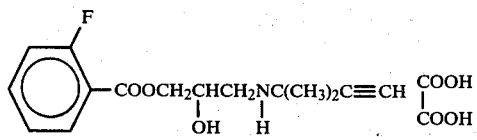

2,3-Epoxypropyl 2-Fluorobenzoate

A mixture containing 37 g (0.5 mole) of glycidol, 500 ml of anhydrous ether, 500 ml of pyridine and 80 g (0.5 mole) of o-fluoro-benzoyl chloride was stirred at 0° C. for 1 hour and 25° C. for 2 hours. The mixture was filtered and the ethanol filtrate was washed with 100 ml of 5% HCl. Evaporation of the ether gave an oil which was distilled to give 69.5 g (71%) of product, b.p. 115° C./0.5 mmHg. The NMR and IR spectra were consistent with the assigned structure.

3-(1,1-Dimethylpropargylamino)-2-hydroxypropyl 2-Fluorobenzoate Oxalate

To 9 g (0.046 mole) of the epoxide from the previous experiment in 50 ml of THF was added 8.5 g (0.092 mole) of 1,1-dimethylpropargylamine. The reaction mixture was refluxed for 16 hours and evaporated to dryness. The residue was dissolved in 100 ml of iPrOH and 6.5 g (0.07 mole) of oxalic acid was added. Addition of 50 ml of ether into the iPrOH solution induced crystallization of the desired product, 3.84 g (23%); m.p. 124°–5°. The NMR and IR spectra were consistent with the assigned structure and elemental analysis was consistent with the empirical formula $C_{17}H_{20}NO_7F$.

EXAMPLE XII

The example describes the synthesis of a compound of the following formula via Method II.

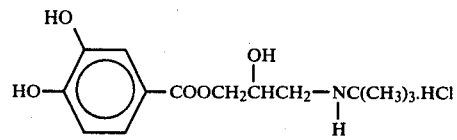

Ethyl 3,4-Dihydroxybenzoate

A mixture which contained 43 g (0.28 mole) of 3,4-dihydroxybenzoic acid, 300 ml of ethanol and 0.5 ml of concentrated $H_2SO_4$ was refluxed for 48 hours. Water was trapped with 3A molecular sieves. The reaction mixture was evaporated to dryness in vacuo, and partitioned between ether and 5% $NaHCO_3$ solution. The ether layer was evaporated to give 39 g (69%) of solid; m.p. 128°–130° C. The NMR and IR spectra were consistent with the assigned structure.

3,4-Dibenzyloxybenzoic Acid

To 60 g (0.33 mole) of ethyl 3,4-dihydroxybenzoate in 50 ml of methyl ethyl ketone was added 105.5 g (0.76 mole) of $K_2CO_3$ and 168.8 g (0.76 mole) of benzyl bromide. The mixture was refluxed for 16 hours and filtered. Evaporation of the filtration gave an oil. This oil was mixed with 40 g of KOH, 350 ml of water and 350 ml of methanol and refluxed for 2.5 hours. The methanol was evaporated and the reaction mixture was acidified with concentrated HCl. The precipitate was filtered to give 101 g (92%) of the desired product; m.p. 184°–5° C. The NMR and IR spectra were consistent with the assigned structure.

3-t-Butylamino-2-hydroxypropyl 3,4-dibenzyloxybenzoate

To 20 g (0.06 mole) of the 3,4-dibenzyloxybenzoic acid in 200 ml of toluene was added 60 g (0.33 mole) of thionyl chloride. The reaction mixture was evaporated to dryness in vacuo to give a solid; m.p. 85°–86°. The solid was dissolved in 100 ml of dry THF and added dropwise into a solution of 17.7 g (0.06 mole) 3-(t-butylamino)-1,2-propanediol in 50 ml of pyridine and 50 ml of toluene. The reaction mixture was stirred for 1 hour at 25° C. and partitioned between ether and 5% $K_2CO_3$ solution. The ether layer was evaporated to dryness to give 30 g of solid.

3-tert-Butylamino-2-hydroxypropyl 3,4-Dihydroxybenzoate Hydrochloride

To 25 g of the dibenzyloxybenzoate obtained from the previous experiment was added 50 ml of ether and acidified with hydrogen chloride. The ether layer was decanted and the oily residue was dissolved in 200 ml of methanol with 2 g of 10% Pd/catalyst. The mixture was agitated for 16 hours under 50 psi of hydrogen. The catalyst was filtered and the filtrate was evaporated to dryness. The product was crystallized in iPrOH to give 14 g (73%) of the product; m.p. 201°–202°. The NMR and IR spectra were consistent with the assigned structure and elemental analysis was consistent with the empirical formula $C_{14}H_{22}NO_5Cl$.

EXAMPLES XIII–XV

The experiment of Example XII was repeated in all essential detail to produce Examples XIII–XV described in Table 2 except that different benzyloxybenzoic acids were used to react with the 3-(-t-butylamino)-1,2-propanediols. Each of the compounds was identified by NMR, IR and elemental analysis.

EXAMPLES XVI AND XVII

The procedure for the preparation of 3-t-butylamino-2-hydroxypropyl 3,4-dibenzyloxybenzoate in Example XII was repeated in all essential detail to produce Example XVII described in Table 2 except that 3,4-dipivaloyloxy benzoic acid was used to react with the 3-(tert-butylamino)-1,2-propanediol. The crude product of Example XVII was chromatographed on silica gel with 10% EtOH in EtoAc to give Example XVI.

The NMR and IR spectra were consistent with the assigned structures. Comparative data relating to Examples XI to XVII are given in Table 2.

EXAMPLE XVIII

The intraocular pressure lowering effect of the compounds described in Examples I–IV and IX–XVII are demonstrated in rabbits with normotensive eyes.

Sterile, isotonic saline solutions of each of the compounds prepared in procedures of Examples I–IV, IX–XVII are prepared by dissolving 10, 30 and 100 mg samples of each of the active compounds in 1 ml of saline to give 1%, 3% and 10% solutions with pH about 6.0–7.0. Free amines require one equivalent of HCl to effect dissolution.

The intraocular pressure lowering effect of each compound is determined by treating the eyes of healthy rabbits with the above solutions. Three rabbits are used to evaluate the effect of each drug concentration. A standard dose of 50 μl of each drug solution is applied to one eye of each of the three rabbits. Intraocular pressure of both eyes is measured with a pressure tonograph or a Mackay-Marg Tonometer before drug administration and at 15, 30, 45, 60, 120, 180, 240, 300, 360, 420 and 480 minutes after dosing. Control rabbits are treated similarly with sterile isotonic saline solution. Intraocular pressure lowering in the treated eyes is compared with the untreated eyes, with saline treated eyes and with predrug pressures. All of the test compounds show intraocular pressure-lowering activity.

EXAMPLE XIX

The experiment of Example XVIII is repeated in all essential details, except that rabbits which have corticosteroid-induced ocular hypertension, as described by Bonomi, L., et al., *Glaucoma*, Eds. R. Pittscrick, A. D. S. Caldwell, Academic Press, New York, pp. 98–107 (1980), are substituted for the normotensive rabbits. Each of the test compounds exhibits intraocular pressure-lowering activity in this model.

TABLE 1

ENZYMATIC HYDROLYSIS OF BETA BLOCKERS BY DOG BLOOD LIVER HOMOGENATE, AND AQUEOUS HUMOR

| | | % HYDROLYZED | | | | | |
|---|---|---|---|---|---|---|---|
| | COM- | | | | | AQUEOUS | |
| | POUND | BLOOD | | LIVER | | HUMOR | |
| EX- | OF | 60 | 120 | 60 | 120 | | 120 |
| AMPLE | EXAMPLE | min | min | min | min | 60 min | min |
| V | III | 100 | 100 | 100 | 100 | 18.9 | 51.9 |
| VI | II | 100 | 100 | 100 | 100 | 21.9 | 61.8 |
| VII | I, Ia | 77.4 | 90.8 | 90.1 | 96.1 | 39.2 | 71.6 |
| VIII | IV | 100 | 100 | 100 | 100 | 61.4 | 100 |

[1]Data at each time point are expressed relative to denatured tissue control.

TABLE 2

$$ArCOOCH_2\overset{OH}{\underset{}{C}}HCH_2-\underset{H}{\overset{}{N}}-R$$

| Example | Ar | R | Method | Yield % | Add. Salt | Crystn. Solvent |
|---|---|---|---|---|---|---|
| XI | 4-F-C₆H₄- | —C(CH₃)₂C≡CH | I | 22.7 | (COOH)₂ | iPrOH—Et₂O |
| XII | 3,4-(HO)₂-C₆H₃- | C(CH₃)₃ | II | 73 | HCl | iPrOH |
| XIII | 3,4-(HO)₂-C₆H₃- | CH(CH₃)₂ | II | 45 | (COOH)₂ | Acetone EtOAC |
| XIV | 3,5-(HO)₂-C₆H₃- | C(CH₃)₃ | II | 58 | HCl | Acetone EtOAC |
| XV | 3,4,5-(HO)₃-C₆H₂- | C(CH₃)₃ | II | 86 | HCl | Acetone |

TABLE 2-continued $$ArCOOCH_2\overset{OH}{\underset{|}{C}H}CH_2-\underset{\underset{H}{|}}{N}-R$$

| Example | Ar | R | Method | Yield % | Add. Salt | Crystn. Solvent |
|---------|-----|-----|--------|---------|-----------|-----------------|
| XVI | 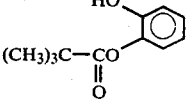 | $C(CH_3)_3$ | II | 3 | — | — |
| XVII | 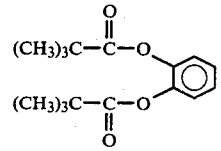 | $C(CH_3)_3$ | II | 21 | — | Oil |

We claim:

1. A method for treating glaucoma or for lowering intraocular pressure in a mammal, which comprises topically applying to the eye of such mammal an intraocular pressure-lowering effective amount of a compound represented by the formula:

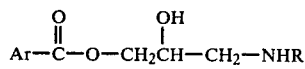

wherein R represents lower alkyl of straight or branched carbon chains from 1 to about 10 carbon atoms; cycloalkyl of from 3 to about 7 carbon atoms; alkenyl of from about 2 to about 10 carbon atoms; alkynyl of from 3 to about 10 carbon atoms; hydroxyalkyl of from 2 to about 7 carbon atoms; aralkyl, wherein the alkyl portion contains from about 1 to about 5 carbon atoms, and the aryl portion represents substituted or unsubstituted monocyclic or polycyclic aromatic of from 6 to about 10 carbon atoms; a group of the formula

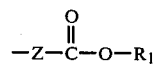

wherein Z represents lower alkylene of straight or branched carbon chains from 1 to about 10 carbon atoms, and $R_1$ is lower alkyl of from 1 to about 5 carbon atoms; and Ar represents substituted or unsubstituted aromatic; or a pharmaceutically acceptable salt thereof.

2. The method of claim 1 wherein R is lower alkyl of from 1 to about 5 carbon atoms; lower alkynyl of from 3 to about 5 carbon atoms; hydroxyalkyl of from 2 to about 5 carbon atoms; or aralkyl wherein the alkyl portion contains from 1 to about 3 carbon atoms and the aryl portion contains from 6 to about 10 carbon atoms, and Ar is unsubstituted phenyl, or phenyl substituted with lower alkyl of from 1 to about 5 carbon atoms, fluoro, chloro, nitro, hydroxy, amino, acyloxy wherein the acyl portion is alkanoyl of from 2 to about 5 carbon atoms, or benzoyl, optionally substituted by halogen, alkoxy, alkyl or hydroxy; or a group of the formula $$R_1-O-\overset{O}{\underset{\|}{C}}-(CH_2)_n-$$

wherein $R_1$ is lower alkyl of from 1 to about 5 carbon atoms and n is an integer from 0 to about 5.

3. The method of claim 1 wherein R is selected from the group consisting of isopropyl, t-butyl, hydroxy-t-butyl, dimethyl propargyl, and 3,4-dimethoxyphenethyl, and Ar is unsubstituted phenyl or phenyl substituted with methyl, fluoro, chloro, nitro, hydroxy, amino, acyloxy, wherein the acyl portion is alkanoyl of from 2 to about 5 carbon atoms, or benzoyl, optionally substituted by halogen, alkyl or hydroxy.

4. The method of claim 1 wherein the applied compound is

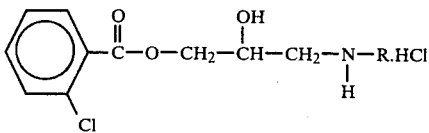

wherein R is isopropyl, t-butyl, hydroxy-t-butyl, dimethylpropargyl or dimethoxyphenethyl.

5. The method of claim 1 wherein the applied compound is

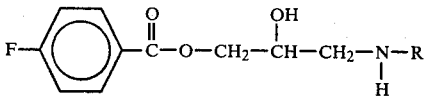

wherein R is isopropyl, t-butyl, hydroxy-t-butyl, dimethylpropargyl or dimethoxyphenethyl.

6. The method of claim 1 wherein the applied compound is

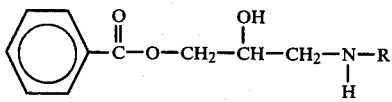

wherein R is isopropyl, t-butyl, dimethylpropargyl, hydroxy-t-butyl or dimethoxyphenethyl.